(12) United States Patent
Hartung et al.

(10) Patent No.: US 7,733,056 B2
(45) Date of Patent: Jun. 8, 2010

(54) PREVENTION OF ELECTRO-CHEMICAL CORROSION AT CHARGING CONTACTS OF A BATTERY-POWERED HANDPIECE AND ITS CHARGER DEVICE

(75) Inventors: Martin G. Hartung, Gilching (DE); Michael Keller, Gauting (DE)

(73) Assignee: 3M Innovative Properties Company, St. Paul, MN (US)

( * ) Notice: Subject to any disclaimer, the term of this patent is extended or adjusted under 35 U.S.C. 154(b) by 304 days.

(21) Appl. No.: 10/828,656

(22) Filed: Apr. 21, 2004

(65) Prior Publication Data

US 2004/0257037 A1    Dec. 23, 2004

(30) Foreign Application Priority Data

Apr. 29, 2003    (EP)    .................. 03009617

(51) Int. Cl.
  *H02J 7/00*    (2006.01)
(52) U.S. Cl. ................ 320/114; 320/108; 320/112; 320/113

(58) Field of Classification Search .................. 320/107, 320/108, 112, 113, 114
See application file for complete search history.

(56) References Cited

U.S. PATENT DOCUMENTS

| | | | |
|---|---|---|---|
| 3,763,434 A | | 10/1973 | Blesch et al. |
| 3,851,322 A | * | 11/1974 | Compoly et al. ............ 340/530 |
| 5,233,283 A | * | 8/1993 | Kennedy .................... 320/115 |
| 5,471,129 A | | 11/1995 | Mann |
| 5,793,186 A | * | 8/1998 | Watabe et al. ............... 320/112 |
| 5,861,729 A | * | 1/1999 | Maeda et al. ............... 320/106 |
| 5,867,798 A | * | 2/1999 | Inukai et al. ................ 455/573 |
| 5,945,809 A | * | 8/1999 | Inaba et al. ................. 320/134 |
| 2001/0000423 A1 | | 4/2001 | Fischer et al. |
| 2002/0074970 A1 | * | 6/2002 | Kawashima ................ 320/107 |

* cited by examiner

*Primary Examiner*—Patrick J Assouad
*Assistant Examiner*—Samuel Berhanu

(57) ABSTRACT

The present invention relates to the prevention of electro-chemical corrosion at charging pins, especially of a battery-powered handpiece and its charging station.

20 Claims, 1 Drawing Sheet

PREVENTION OF ELECTRO-CHEMICAL CORROSION AT CHARGING CONTACTS OF A BATTERY-POWERED HANDPIECE AND ITS CHARGER DEVICE

This application claims priority from EP Application No. 03009617.6, filed Apr. 29, 2003.

FIELD OF THE INVENTION

The present invention relates to the prevention of electro-chemical corrosion at charging contacts, in particular at charging contacts of a battery-powered handpiece and its charger device, especially in the presence of electrically conductive fluids, such as disinfectants.

BACKGROUND OF THE INVENTION

In different fields of application, battery-powered handpieces and their charging stations are necessarily in contact with liquids, and there is a need to protect electrical contacts of such battery-powered handpieces and their charging stations from liquids, or to keep the contacts dry. User manuals or labels of such battery-powered devices give instructions to the user as to avoid liquids and to keep the contacts dry. However, it can be experienced that in current practice, these instructions are not considered or followed in every case. Furthermore, fluid films on the contacts may be present even if these instructions are complied with because fluid films are not necessarily visually observable. For example by wiping the battery-powered device and its charger device with a moist cloth, the remaining liquid film may still be sufficient to cause some weak corrosion, even if the fluid or agent vaporises after a few minutes. If a longer period of time is considered, the incremental corrosion of the contacts will affect the electrical properties of the contacts.

Unlike contacts at commonly used plugs, it is not useful to protect charging contacts of battery-powered electrical devices by sealing covers or means that would protect them from liquids that may be used in combination with such devices. It is rather useful and desirable that such charging contacts are open and easily accessible because placing the battery-powered device into the charging station and the charging operation should be easy and quick. Such contacts are typically realised by metallic elements on one component, e.g., the handpiece, and are placed somewhere at the surface of the housing. The other component, e.g., the charging station, may have metallic pins or stripes or the like sticking out of the housing of the charging station in order to allow a proper electrical contact whenever the handpiece is placed into the charger station. Thus, fluids used with the device may flow to the charging contacts, and in particular in the region of the housing separating the contacts. Furthermore, if these fluids are electrically conductive, an electric current may flow between the contacts. This currents initiate an electro-chemical reaction which in turn leads to a corrosion of the contacts. Corroded contacts, in turn, result in increased contact resistances. Significant electrical power will drop at the contacts and heat them up. The increased resistance will affect a proper charging procedure, and will in the end totally hinder the re-charging of the battery.

The presence of such fluids is quite common, especially with electro-medical devices, such as dental curing lights, since such devices are treated with cleaning or disinfectant agents quite frequently.

SUMMARY OF THE INVENTION

It is thus an object of the present invention to provide for a prevention of electro-chemical corrosion of electric contacts, in particular of a battery-powered handpiece and its charger device. This object is achieved with the features of the claims.

In one aspect, the invention provides a battery-powered handpiece comprising a first charging contact connectable to a first contact of a battery and means for allowing charging current to flow from said first charging contact into said battery but preventing current flow in opposite direction.

Even if the battery-containing device, i.e. the battery-powered handpiece, is not placed into the charger device, electro-chemical corrosion may occur if the handpiece is treated with, e.g., disinfectants. Such agents may result in a more or less extensive fluid film between the charging contacts. As the battery voltage is present at the contacts, a current may flow through the film. Over a certain period of time, this current leads to a corrosion of the metal surface of the contacts. A means for allowing charging current to flow from a first charging contact into a battery but preventing current flow in opposite direction is inserted between said first charging contact and the battery. Preferably, the means for allowing charging current to flow from said first charging contact into said battery but preventing current flow in opposite direction is a semiconductor diode. The diode is oriented in such a way that the charging current may flow from the charger over the charging contact towards the battery; however, the diode prevents any current from flowing into the opposite direction, which would be the case if fluids were present between the charging contacts.

Preferably, the battery-powered handpiece further comprises a second charging contact connectable to a second contact of a battery.

In a preferred embodiment, the battery-powered handpiece comprises a sensing contact arranged in the path of potential electrolytic current flow between the first charging contact and the second charging contact. In case fluids are present between the charging contact of the battery-powered handpiece, the current circuit over the battery will be closed, and electrolytic current flow will occur between the two charging contacts. The additional sensing contact is provided for sensing such electrolytic current flow. If such electrolytic current flow is detected by the sensing contact, a warning signal may be given to the user of the handpiece. The additional sensing contact provides an additional safety feature for detecting electrolytic current flow.

The battery-powered handpiece may further comprise a magnetic means that cooperates with a magnetically activatable switch provided in a charger device to initiate a charging operation once the handpiece is electrically connected to the charger device.

Preferably, the magnetic means is a magnet that is arranged in the proximity of the housing of the handpiece. If the handpiece is inserted into the charger device in order to start a charging operation, the magnet cooperates with the magnetically activatable switch provided in the charger device and activates the switch to initiate a charging operation.

According to another aspect of the invention, a charger device for a battery-powered handpiece is provided. The charger device comprises a detector for detecting the presence or absence of said handpiece, and a switch for switching on/off the charging voltage dependent on a detection of the presence/absence of said handpiece.

Typically, a voltage is present at the contacts of the charger device even if the battery-powered handpiece is not placed into the same. A fluid film between the charging pins of the charger device would result in a current that causes corrosion. Prevention of corrosion can be achieved in that the charging voltage is disconnected from the charging pins of the charger device whenever the handpiece is not present.

Preferably, mechanical switches, optical, electromechanical switches, electro-optical switches, or magnetic switching means (e.g., magnetic switches, sensors or switches) are used. For example, if the handpiece comprises a magnetic means (e.g., a magnet), the charger device comprises a magnetic sensor comprising a magnetically activatable switch that is operable in response to the magnetic field of the handpiece. More preferably, the magnetically activatable switch is a Reed switch that closes the voltage circuit to the charging pins of the charger device as soon as the handpiece is placed into the charger device.

More preferably, the charger device comprises a first charging pin and a second charging pin. The switch allows a charging voltage to be applied to said charging pins in the presence of said handpiece.

More preferably, the charger device comprises a sensing pin arranged in the path of potential electrolytic current flow between the first charging pin and the second charging pin. The sensing pin detects a potential electrolytic current flow between the first and second charging pins.

In a preferred embodiment, the charger device for a battery-powered handpiece comprises a first charging pin, a second charging pin and a sensing pin arranged in the path of potential electrolytic current flow between said first charging pin and said second charging pin. The sensing pin detects electrolytic current between said first and second charging pins.

If a fluid film is present between the charging pins of the charger device, the result will be corrosion, as now the charging current is flowing, which in turn results in a voltage between the charging pins. The additional pin, i.e. a sensing pin, is placed between the plus and minus charging pins of the charger device. If an electrolytic current is flowing between the charging pins, a certain voltage drop will be present at this additional sensing pin. Preferably, a sensing voltage with a sufficiently high impedance is applied to the pins before the actual charging current is switched on. If a liquid film and, as a result, a voltage at the additional sensing pin is present, the charging circuit of the charger device will not switch on the charging current. Preferably, in this case, a warning signal is given to the user, for example an acoustic and/or optical signal that indicates to the user that there is still liquid between the pins that is to be removed by dry-wiping etc.

Furthermore, according to a preferred embodiment, the sensing pin provided at the charger device is in contact with the additional sensing contact provided between the charging contacts at the handpiece. By this means, it is not only possible to detect electrolytic current between the charging pins of the charger device but also between the charging contacts at the handpiece. Thus, liquid films on the charger device and on the handpiece can be detected by the charger device.

More preferably, the charger device comprises an electronic switch connected to the sensing pin of the charger device. The electronic switch is responsive to a voltage signal detected at the sensing pin of the charger device, and disconnects a charging voltage applied to the first and second charging pins if electrolytic current flow is sensed by the sensing pin.

In yet another aspect, the invention provides a battery-powered handpiece in combination with a charger device.

The corrosion prevention means of the present invention guarantees a trouble-free operation of the entire assembly with proper charging of the battery even if extensive amounts of, e.g., disinfectants are used. Devices equipped with a corrosion prevention according to the present invention are more user-friendly.

BRIEF DESCRIPTION OF THE DRAWINGS

The present invention will now be described in more detail with reference to the drawing.

DETAILED DESCRIPTION OF THE DRAWINGS

Figure 1:
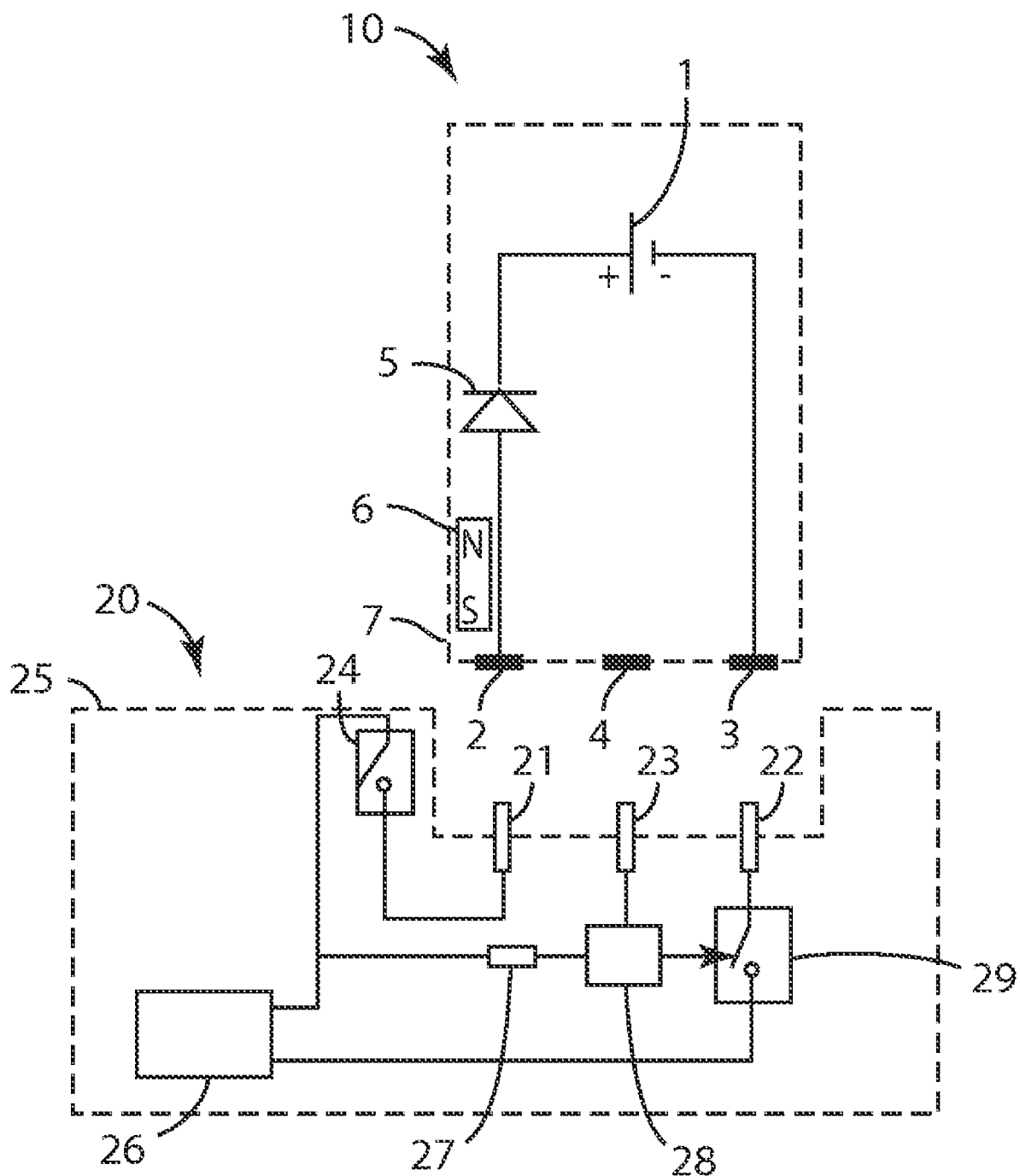
FIG. 1 shows in schematic form a battery-powered handpiece and a charger device/charging station of the invention.

A preferred battery-powered handpiece 10 as shown in FIG. 1 comprises a battery 1 as well as two charging contacts 2, 3. Between the first charging contact and the battery, a diode 5 is arranged that allows current flow from the charging contact to the battery but not in opposite direction.

In close proximity to a housing 7 of the battery-powered handpiece 10, a magnet 6 is provided. This magnet cooperates with a Reed switch 24 arranged in proximity of the housing 25 of a charging station 20. The Reed switch 24 of the charging station 20 and the magnet 7 of the handpiece 10 are arranged within the respective housings such that they are close to each other once the handpiece is placed into the charging station 20 so that the magnetic field of the magnet 6 causes a response of the Reed switch 24. Once the magnet is close to the Reed switch 24, the switch closes, and the charging circuit, i.e. the charging voltage, is applied to charging pins 21, 22 of the charging station 20.

The charging station 20 further comprises an additional sensing pin 23 arranged between the charging pins 21, 22 of the charging station 20. The sensing pin 23 is also connected to a charging circuit 26 of the charging station via a resistor 27 and a control circuit 28 so that a sensing voltage with a sufficiently high impedance can be applied to the sensing pins 23 before the charging voltage is applied. The control circuit 28 controls an electronic switch 29. If an electrolytic current flow between the charging pins 21, 22 is detected by the sensing pin 23, the control circuit 28 causes the electronic switch 29 to not close the charging circuit, or to open the charging circuit if it is already closed.

The battery-powered handpiece 10 further comprises an additional sensing contact 4. The additional sensing contact 4 of the battery-powered handpiece 10 is arranged in the path of a potential electrolytic current flow between the charging contacts 2, 3. If the handpiece 10 is placed into the charging station 20, the additional sensing contact 4 of the handpiece 10 is in contact with the sensing pin 23 of the charging station 20, and any current flow between the charging contacts of the handpiece is detected by the sensing pin 23 of the charging station 20, and will cause a signal to the control circuit and an interruption of the charging circuit by means of the electronic switch 29.

The invention claimed is:
1. Battery-powered handpiece, comprising:
(a) a housing;
(b) first and second charging contacts exposed on the housing, for connection to contacts of a battery contained within the housing; and

(c) a sensing contact positioned on the housing for detecting electrolytic current flow through a fluid film on the housing between the first charging contact and the second charging contact.

2. Battery-powered handpiece according to claim 1, further comprising a magnet co-operating with a magnetically activatable switch arranged in a charger device, for initiating a charging operation once the battery-powered handpiece is electrically connected to said charger device.

3. Battery powered handpiece according to claim 2, wherein said magnet is arranged in proximity to the housing of the handpiece.

4. Battery-powered handpiece according to claim 1, further comprising a diode located between said first charging contact and said first contact of said battery for allowing charging current to flow from said first charging contact into said battery but preventing current flow in opposite direction.

5. In combination, a battery powered handpiece according to claim 1 and a charger device comprising: (a) a charger housing;
(b) first and second charging pins exposed on the charger housing and adapted to contact charging contacts on a handheld device; and
(c) a sensing pin on the housing for detecting at least one of (i) electrolytic current flow through a fluid film on the housing between the first charging pin and the second charging pin; and (ii) electrolytic current flow through a fluid film on the housing of a handheld device that is detected by a sensing contact of the handheld device.

6. Battery-powered handpiece according to claim 1, wherein said handpiece is a dental tool.

7. Battery-powered handpiece according to claim 6, wherein said dental tool is dental curing light.

8. Charger device for a battery-powered handpiece, comprising:
(a) a housing;
(b) first and second charging pins exposed on the housing and adapted to contact charging contacts on a handheld device; and
(c) a sensing pin on the housing for detecting at least one of (i) electrolytic current flow through a fluid film on the housing between the first charging pin and the second charging pin; and (ii) electrolytic current flow through a fluid film on the housing of a handheld device that is detected by a sensing contact of the handheld device.

9. Charger device according to claim 8, further comprising a warning means for giving a warning signal if current flow between said first and second charging pins is sensed by said sensing pin.

10. Charger device according to claim 9, wherein said warning means provides an acoustic and/or optical warning.

11. Charger device according to claim 8, wherein said sensing pin of said charger device is in contact with a sensing pin at said handpiece if said handpiece is connected to the charger device so that said sensing pin at said charging device further detects current flow between first and second charging contacts of said handpiece, said current flow having a potential for initiating an electrochemical reaction.

12. Charger device according to claim 8, further comprising an electronic switch connected to said sensing pins of said charger device for disconnecting a charging voltage applied to said first and second charging pins if current flow is sensed by said sensing pin.

13. Charger device according to claim 8, further comprising a detector for detecting the presence or absence of said battery-powered handpiece and a switch for switching on/off the charging voltage dependent on detection of the presence/absence of said handpiece.

14. Charger device according to claim 13, wherein said switch is selected from the group comprising mechanical switches, optical switches, electro-mechanical switches, electro-optical switches or magnetic switches.

15. Charger device according to claim 14, wherein the magnetic switch comprises a magnetically activatable switch being operable in response to a magnet arranged in said handpiece.

16. Charger device according to claim 15, wherein said magnetically activatable switch comprises a Reed switch.

17. Charger device according to claim 13, said switch allowing a charging voltage to be applied to said charging pins in the presence of said handpiece.

18. Charger device according to claim 8 adapted for use with a dental tool.

19. Charger device according to claim 18, wherein said dental tool is dental curing light.

20. In combination:
A. a battery-powered handpiece, comprising:
(i) a housing;
(ii) first and second charging contacts exposed on the housing, for connection to contacts of a battery contained within the housing; and
(iii) a sensing contact positioned on the housing for detecting electrolytic current flow through a fluid film on the housing between the first charging contact and the second charging contact; and
B. a charger device for the battery-powered handpiece, comprising:
(i) a housing;
(ii) first and second charging pins exposed on the housing and adapted to contact charging contacts on the handheld device; and
(iii) a sensing pin on the housing for detecting at least one of (a) electrolytic current flow through a fluid film on the housing between the first charging pin and the second charging pin; and (b) electrolytic current flow through a fluid film on the housing of a handheld device that is detected by a sensing contact of the handheld device.

* * * * *